(12) United States Patent
Hrabie et al.

(10) Patent No.: US 6,949,530 B2
(45) Date of Patent: Sep. 27, 2005

(54) NITRIC OXIDE-RELEASING AMIDINE DIAZENIUMDIOLATES, COMPOSITIONS AND USES THEREOF AND METHOD OF MAKING SAME

(75) Inventors: Joseph A. Hrabie, Frederick, MD (US); Larry K. Keefer, Bethesda, MD (US); Ernst V. Arnold, Hagerstown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 61 days.

(21) Appl. No.: 10/198,242

(22) Filed: Jul. 18, 2002

(65) Prior Publication Data

US 2004/0014720 A1 Jan. 22, 2004

(51) Int. Cl.[7] ...................... A61K 31/655; C07C 245/24
(52) U.S. Cl. ...................... 514/149; 514/647; 514/649; 534/550; 534/566
(58) Field of Search ............................... 514/149, 647, 514/649; 534/550, 566

(56) References Cited

U.S. PATENT DOCUMENTS

| | | |
|---|---|---|
| 4,954,526 A | 9/1990 | Keefer |
| 5,155,137 A | 10/1992 | Keefer et al. |
| 5,212,204 A | 5/1993 | Keefer et al. |
| 5,674,894 A | 10/1997 | Currie et al. |
| 5,770,645 A | 6/1998 | Stamler et al. |
| 6,232,336 B1 | 5/2001 | Hrabie et al. |

FOREIGN PATENT DOCUMENTS

| | | |
|---|---|---|
| WO | WO 93/13055 | 7/1993 |
| WO | WO 94/27957 | 12/1994 |
| WO | WO 96/36639 | 11/1996 |
| WO | WO 96/40665 | 12/1996 |

OTHER PUBLICATIONS

Arnold et al., *Tetrahedron Letters*, 41, 8421–8424 (2000).
Boschi et al., *Bioorg. & Med. Chem.*, 8, 1727–1732 (2000).
Database Search, Derwent Publications, Ltd., "New, N,N'–dihydroxydiazenum Propanol Derivs.—For Prevention and Treatment of Apple Canker," (Jan. 14, 1985).
Etchenique et al., *J. Am. Chem. Soc.*, 122, 3967–3968 (2000).
Freeman et al., *J. Org. Chem.*, 35(9), 3107–3110 (1970).
Hrabie et al., *Bioconjugate Chem.*, 10, 838–842 (1999).
Severina et al., *Biochem. and Mol. Bio. Int.*, 36(4), 913–925 (Jul. 1995).
Soulère et al., *Bioorg. Med. Chem. Lett.*, 10(12), 1347–1350 (2000).
Southan et al., *Nitric Oxide: Bio. and Chem.*, 2(4), 270–286 (1998).
Volodarskii et al., *Chem. Abstr.*, 85(21), 505 (1976).

*Primary Examiner*—Kamal A. Saeed
(74) *Attorney, Agent, or Firm*—Leydig, Voit & Mayer, Ltd.

(57) ABSTRACT

The present invention relates to nitric oxide-releasing amidine diazeniumdiolates, compositions comprising same, methods of using same, and a method for preparing same from imidate diazeniumdiolates and primary or secondary amines.

16 Claims, No Drawings

NITRIC OXIDE-RELEASING AMIDINE DIAZENIUMDIOLATES, COMPOSITIONS AND USES THEREOF AND METHOD OF MAKING SAME

FIELD OF THE INVENTION

The invention relates to nitric oxide-releasing amidine diazeniumdiolates, compositions comprising same, methods of using same, and a method for preparing same from imidate diazeniumdiolates.

BACKGROUND OF THE INVENTION

Nitric oxide (NO) has been implicated as part of a cascade of interacting agents involved in a wide variety of bioregulatory processes, including the physiological control of blood pressure, macrophage-induced cytostasis and cytotoxicity, and neurotransmission (Moncada et al., "Nitric Oxide from L-Arginine: A Bioregulatory System," *Excerpta Medica*, International Congress Series 897, Elsevier Science Publishers B.II.: Amsterdam (1990); Marletta et al., *Biofactors* 2: 219–225 (1990); Ignarro, *Hypertension (Dallas)* 16: 477–483 (1990); Kerwin et al., *J. Med. Chem.* 38: 4343–4362 (1995); and Anggard, *Lancet* 343: 1199–1206 (1994)). Given that NO plays a role in such a wide variety of bioregulatory processes, great effort has been expended to develop compounds capable of releasing NO. Some of these compounds are capable of releasing NO spontaneously, e.g., by hydrolysis in aqueous media, whereas others are capable of releasing NO upon being metabolized (Lefer et al., *Drugs Future* 19: 665–672 (1994)).

Keefer et al. (U.S. Pat. Nos. 4,954,526; 5,039,705; 5,155,137; 5,208,233 and 5,405,919 and related patents and patent applications, all of which are incorporated herein by reference) disclose, among others, the use of certain nucleophile/nitric oxide adducts as NO-releasing agents, i.e.,

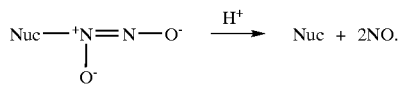

in which the nucleophile residue (Nuc) is a primary amine, a secondary amine or a polyamine. Although such adducts offer many advantages over other currently available nitric oxide-releasing compounds, one disadvantage presented by the use of such adducts as pharmaceutical agents is the potential risk of release of nitrosamines, which are carcinogenic, upon decomposition and release of NO. Another disadvantage of the adducts of primary amines is that they can be unstable even as solids due to a tendency to form traces of potentially explosive diazotates.

Several types of compounds of the general structure

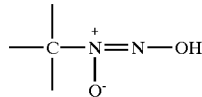

have been known for many years. See Hrabie and Keefer, *Chem. Rev.* 102, 1135–1154 (2002) for a review of diazeniumdiolate chemistry. Traube (*Liebigs Ann. Chem.* 300: 81–123 (1898)) reported the preparation of a number of such compounds and noted that treatment of the compounds with acid produced a "brown gas." Although brown gas suggests the release of NO, given that a brown gas also may be produced in the disproportionation of nitrite, the release of brown gas by the compounds prepared by Traube is not, in and of itself, evidence of NO release. Compounds of the structural type reported by Traube are known to require harsh treatment with mineral acids to release any gas, which is incompatible with a biological utility.

Another compound, named cupferron, of the structure

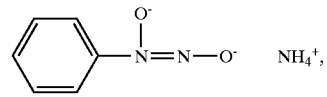

has been shown by Kubrina et al., *Izvestia Akademii Nauk SSSR Seriia Biologicheskaia* 6: 844–850 (1988)) to generate NO in vivo. In addition, the antibiotics alanosine (C(O)(OH)CH(NH$_2$)CH$_2$ N(O)=NOH) and dopastin (CH$_3$CH=CHC(O)NHCH$_2$ CH(i-propyl)-N(O)=NOH), as well as cupferron, have been shown to release NO in vivo by enzymatic oxidation (Alston et al., *J. Biol. Chem.* 260: 4069–4074 (1985)).

More recently, Keefer et al., in U.S. Pat. No. 5,212,204, broadly described that an organic moiety may be linked via a carbon to the N$_2$O$_2^-$ group. This patent does not disclose an amidine structure as the nucleophile, nor does it teach the nature of the structural characteristics that an organic moiety must possess such that the resulting N$_2$O$_2^-$ group is a nitric oxide donor.

In this regard, a recent study of the N$_2$O$_2^-$ group (Taylor et al., *J. Org. Chem.* 60: 435–444 (1995)) proposed a mechanism for the observed NO release. The proposed mechanism was based on quantum mechanical calculations, which showed protonation at the terminal oxygen to be most favored thermodynamically in the case of N bound N$_2$O$_2^-$.

None of the above disclosures, however, mention anything about the release of nitroxyl (HNO, which, at the physiological pH of 7.4, exists as NO$^-$) by this functional group. Recent results suggest that, under certain conditions, many classes of "NO donors" may release some NO$^-$ (see the discussions for nitrosothiols and diazeniumdiolates as well as the table of NO donors in Feelisch et al., Donors of Nitrogen Oxides, *Methods in Nitric Oxide Research*, M. Feelisch and J. S. Stamler, Eds., Ch. 7, pp. 71–115, John Wiley and Sons, New York (1996)).

To date, there are three compounds used to generate HNO in solution. One compound, Angeli's salt, which is the standard HNO source (Fukuto et al., *J. Pharm. Exp. Ther.* 263: 546–551 (1992)), is an inorganic salt. The other two compounds, acetylated Piloty's acid (Smith et al., *J. Amer. Chem. Soc.* 82: 5731–5740 (1960)) and benzoylated hydroxycyanamide (Lee et al., *J. Med. Chem.* 35 3648–3652 (1992)) are promising inhibitors of aldehyde dehydrogenase. However, even in these compounds, there is debate as to whether the observed physiological effects are attributed to NO, or to NO$^-$. For example, Piloty's acid has been shown to release NO oxidatively under physiological conditions (Zamora et al., *Biochem. J.* 312: 333–339 (1995)).

Reports that superoxide dismutase can prolong the effects of NO via its reversible reduction to NO$^-$ (Murphy et al., *PNAS USA* 88: 10860–10864 (1991)) and that NO$^-$, itself, exhibits potent activity as a vasodilator (Fukuto et al., *J. Pharm. Exp. Ther.* 263: 546–551 (1992)) and as an inhibitor of aldehyde dehydrogenase (Lee et al., *J. Med. Chem.* 35: 3648–3652 (1992)) suggest that compounds, which release either NO or NO- or mixtures of the two, are potentially useful pharmaceutical agents and may even offer advantages over compounds that just release NO.

Despite the extensive literature available on NO and nitric oxide-releasing compounds, there remains a need for stable nitric oxide-releasing compounds in which the nitric oxide-releasing group $N_2O_2^-$ is bonded directly to a carbon atom and which can be prepared from compounds that do not include a nitrogen atom suitable for conversion to a diazeniumdiolate. Moreover, because not all compounds, such as proteins, are stable to direct treatment with nitric oxide, there is a need for other synthetic routes that enable the production of a previously inaccessible class of compounds. These and other objects of the present invention, as well as additional inventive features, will be apparent from the description of the invention provided herein.

BRIEF SUMMARY OF THE INVENTION

The present invention provides NO- or NO$^-$-releasing amidine diazeniumdiolates in which the $N_2O_2^-$ functional group is bonded to a carbon atom. The present invention also provides compositions comprising such diazeniumdiolate compounds, and methods of using such compounds and compositions. The present invention further provides a method of producing an NO- or NO$^-$-releasing amidine diazeniumdiolate derived from an imidate diazeniumdiolate.

DETAILED DESCRIPTION OF THE INVENTION

The present invention provides novel nitric oxide-releasing amidine compounds of Formula I:

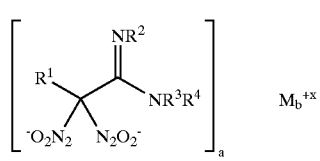

wherein $R^1$ is an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted $C_{1-12}$ alkoxy, nitrile, halo, an unsubstituted or substituted benzyl, an unsubstituted or substituted phenyl, an unsubstituted or substituted piperazino, an unsubstituted or substituted morpholinyl, amino, an unsubstituted or substituted $C_{1-12}$ alkylamino, an unsubstituted or substituted $C_{6-30}$ arylamino, an unsubstituted or substituted $C_{1-12}$ dialkylamino, an unsubstituted or substituted $C_{6-30}$ diarylamino, carboxy-$C_{1-12}$ alkylamino, carboxy-$C_{1-12}$ dialkylamino, an unsubstituted or substituted tolyl, xylyl, anisyl, mesityl, an unsubstituted or substituted acetoxy, carboxy, an unsubstituted or substituted carboxyethyl, an unsubstituted or substituted $C_{1-12}$ alkylcarbonyl, thio, an unsubstituted or substituted $C_{1-12}$ alkylthio, an unsubstituted or substituted $C_{1-12}$ alkyloxy, carboxamido, an unsubstituted or substituted $C_{1-12}$ alkylcarboxamido, an unsubstituted or substituted $C_{1-12}$ dialkylcarboxamido, an unsubstituted or substituted phenoxy, an unsubstituted or substituted benzyloxy, phenylcarbonyl, benzylcarbonyl, an unsubstituted or substituted nitrophenyl, $C_{1-12}$ trialkylsilyl or nitro; $R^2$, $R^3$, and $R^4$ are the same or different and are selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted $C_{3-8}$ cycloalkyl, a $C_{3-8}$ heterocyclic ring, an unsubstituted or substituted naphthyl, an unsubstituted or substituted tetrahydronaphthyl, an unsubstituted or substituted octahydronaphthyl, benzyl or substituted benzyl, phenyl or substituted phenyl, polymer, adenine, guanine, cytosine, thymine, protein, enzyme, nucleotide, oligonucleotide, nucleoside, peptide, polypeptide, and amino acid; $M^{+x}$ is a pharmaceutically acceptable cation, x is the valence of the cation, and a and b are the smallest integers that result in a neutral compound.

Preferably, $R^1$ of the compound of Formula I is an unsubstituted or substituted aryl. More preferably, $R^1$ of the compound of Formula I is an unsubstituted or substituted phenyl, and most preferably $R^1$ of the compound of Formula I is phenyl, 4-methoxyphenyl, 4-chlorophenyl, or 3,4,5-trimethoxyphenyl. Preferably, $R^2$ of the compound of Formula I is hydrogen or $R^2$ and $R^3$ are both hydrogen. Preferably, $R^4$ is a moiety other than hydrogen.

Any one or more of $R^1$, $R^2$, $R^3$, and $R^4$ of Formula I can be substituted. Generally each of $R^1$, $R^2$, $R^3$, and $R^4$ can have 1 to 10 substituents (e.g., 1 to 8, 1 to 6, 1 to 4, 1 to 3 substituents) that are independently selected from the group consisting of $C_{1-12}$ alkyl, $C_{6-30}$ aryl, $C_{1-12}$ alkoxy, $C_{1-12}$ aryloxy, acyloxy, benzyl, benzyloxy, acetyl, carboxyl, carboxy-$C_{1-12}$ alkyl, carboxy-$C_{1-12}$ alkylamido, carboxy-$C_{1-12}$ dialkylamido, carboxamido, $C_{1-12}$ alkylcarbonyl, $C_{6-30}$ arylamino, $C_{6-30}$ diarylamino, nitrile, tolyl, xylyl, mesityl, anisyl, pyrrolidinyl, formyl, dioxanyl, $C_{1-12}$ alkylthio, $C_{5-30}$ heteroaryl, such as pyranyl, pyrrolyl, furanyl, thiophenyl, thiazolyl, pyrazolyl, pyridinyl, or pyrimidinyl, phenylcarbonyl, benzylcarbonyl, nitrophenyl, $C_{1-12}$ trialkylsilyl, nitro, sulfonyl, nitrobenzyl, $C_{1-12}$ trialkylammonium, tetrahydrofuranyl, tetrahydropyranyl, piperdinyl, morpholinyl, halo, cyano, hydroxy, thio, $C_{3-8}$ cycloalkyl, amino, $C_{1-12}$ alkylamino, $C_{1-12}$ dialkylamino and diazeniumdiolato ($N_2O_2^-$).

The counterion, $M^{+x}$, is any pharmaceutically acceptable counterion. The only requirement for the pharmaceutically acceptable counterion chosen is biological compatability in a mammal, such as a human. Biologically acceptable counterions include alkali metals such as sodium ion, potassium ion, lithium ion, and the like; alkaline earth metals such as magnesium ion, calcium ion, and the like; Group III metals such as aluminum ion; Group I metals such as tin ion; and transition metals, including iron ion, copper ion, manganese ion, zinc ion, cobalt ion, vanadium ion, molybdenum ion, platinum ion, and the like. Non-metal counterions include quaternary ammonium ions. Metal ions that may be considered toxic may, nevertheless, be pharmaceutically acceptable and thus within the scope of the invention if their complexes with the diazeniumdiolates are sufficiently potent pharmacologically and the total concentration of the metal counterion upon dosing is below the toxic threshold of the metal.

The present invention also includes a polymer-bound compound of Formula Ia:

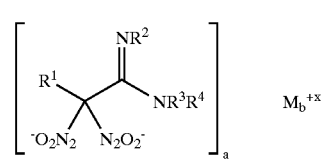

wherein $R^1$, $R^2$, and $R^3$ are as described herein for Formula (I), and $R^4$ is a polymer. $R^4$ is any suitable polymer, such as polyolefins, such as polystyrene, polypropylene, polyethylene, polytetrafluorethylene, polyvinyl chloride, polyvinylidene difluoride, and polyethers such as polyethylene glycol, polysaccharides such as dextran, polyesters such as poly(lactide/glycolide), polyamides such as nylon, polyurethanes, polyethylenimine, biopolymers such as peptides, polypeptides, enzymes, polysaccharides, proteins, oligonucleotides, antibodies and nucleic acids, starburst dendrimers, copolymers and mixtures thereof. For example, chitosan is a polysaccharide containing numerous primary amine groups. The term "biopolymers", as used herein, also include monomeric units of larger biopolymers such as monosaccharides, amino acids or nucleotides.

Any of the substituents can be substituted with a diazeniumdiolato group. Preferably, the nitric oxide-releasing-substituted group is that of a polymer ($R^4$ in the case of compounds of Formula (Ia)), e.g., a nitric oxide-releasing amidine bound to a polymer, similar to those described in, for example, U.S. Pat. Nos. 5,405,919, 5,525,357, 5,632, 981, 5,650,447, 5,676,963, 5,691,423, and 5,718,892, and incorporated herein by reference. By "bound to a polymer" it is meant that the nitric oxide-releasing amidine, such as those described by Formulae I and Ia is associated with, part of, incorporated with, or contained within the polymer matrix physically or chemically. Physical association or bonding of the nitric oxide-releasing amidine to the polymer may be achieved by co-precipitation of the polymer with the nitric oxide-releasing amidine as well as by covalent bonding of the complex to the polymer. Chemical bonding of the nitric oxide-releasing amidine to the polymer may be by, for example, covalent bonding of the amino moiety of the nitric oxide-releasing amidine to the polymer such that the amidine residue to which the $NONO^-$ group is attached forms part of the polymer itself, i.e., is in the polymer backbone, or is attached to a group or groups pendant to the polymer backbone. If the diazeniumdiolates of the present invention are chemically bound to the polymer/biopolymer, then the diazeniumdiolates are bound to the polymer/biopolymer by at least one functional group on the polymer or biopolymer. Preferably, more than one diazeniumdiolate compound of the present invention is chemically bound per molecule of the polymer/biopolymer. The manner in which the nitric oxide-releasing amidine is associated, part of, or incorporated with or contained within, i.e., "bound" to the polymer, is inconsequential to the invention and all means and degrees of association, incorporation or bonding are contemplated herein.

The advantage of preparing diazeniumdiolate compounds bound to a (bio)polymer by the methods of the present invention is that the diazeniumdiolate compound is formed first and then bound to the polymer. These methods enable a whole new class of compounds to be prepared because the (bio)polymer is not directly exposed to the potentially deleterious effects of nitric oxide gas or any other nitrogen oxide that might form therefrom in the presence of oxygen.

Another aspect of this invention includes a method for preparing a nitric oxide-releasing amidine that is capable of being bound to a substrate, where the method includes contacting the diazeniumdiolate with a substrate. Preferably the substrate has moieties that allow for chemical bonding of the NO-releasing amidine to the substrate. See, for example, U.S. Pat. No. 6,270,779, which is incorporated herein in its entirety. The NO-releasing amidines can be in contact with the substrate in any suitable association, such as, for example, form part of the substrate, be bound to the substrate, or be coated onto the substrate.

The substrate can be of any suitable biocompatible material, such as metal, glass, ceramic, or plastic or rubber. Preferably, the substrate is metal. The substrate used in the preparation of the medical device can be derived from any suitable form of a biocompatible material, such as, for example, a sheet, a fiber, a tube, a fabric, an amorphous solid, an aggregate, dust or the like.

Metal substrates suitable for use in the invention include, for example, stainless steel, nickel, titanium, tantalum, aluminum, copper, gold, silver, platinum, zinc, silicon, magnesium, tin, alloys, coatings containing any of the above and combinations of any of the above. Also included are such metal substrates as galvanized steel, hot dipped galvanized steel, electrogalvanized steel, annealed hot dipped galvanized steel and the like. Preferably, the metal substrate is stainless steel.

Glass substrates suitable for use in the invention include, for example, soda lime glass, strontium glass, borosilicate glass, barium glass, glass-ceramics containing lanthanum as well as combinations thereof.

Ceramic substrates suitable for use in the invention include, for example, boron nitrides, silicon nitrides, aluminas, silicas, combinations thereof, and the like.

Plastic substrates suitable for use in the invention include, for example, acrylics, acrylonitrile-butadiene-styrene, acetals, polyphenylene oxides, polyimides, polystyrene, polypropylene, polyethylene, polytetrafluoroethylene, polyvinylidene, polyethylenimine, polyesters, polyethers, polylactones, polyurethanes, polycarbonates, polyethylene terephthalate, as well as copolymers and combinations thereof. Typical rubber substrates suitable for use in the invention include, for example, silicones, fluorosilicones, nitrile rubbers, silicone rubbers, fluorosilicone rubbers, polyisoprenes, sulfur-cured rubbers, isoprene-acrylonitrile rubbers, and the like. Silicones, fluorosilicones, polyurethanes, polycarbonates, polylactones, and mixtures or copolymers thereof are preferred plastic or rubber substrates because of their proven bio- and hemocompatability when in direct contact with tissue, blood, blood components, or bodily fluids.

Other suitable substrates include the silane coatings described in WO 00/63462, and incorporated herein by reference.

The invention provides medical devices which are capable of releasing nitric oxide when in use, but which are otherwise inert to nitric oxide release. In particular, NO-releasing functional groups can be part of, bound to, or coated on a substrate with a compound of Formulae (I) or (Ia). The term "bound" as used herein includes covalent bonds, ionic bonds, van der Waal forces, hydrogen bonding, electrostatic bonding, and all other methods for attaching organic chemical functional groups to a substrate.

A "medical device" refers to any device having surfaces that contact tissue, blood, or other bodily fluids in the course of their use or operation, which are found in or are subsequently used in patients or animals. Medical devices include, for example, extracorporeal devices for use in surgery, such as blood oxygenators, blood pumps, blood storage bags, blood collection tubes, blood filters including filtration media, tubing used to carry blood and the like which contact blood which is then returned to the patient or animal. Medical devices include wound dressing, as well. Medical devices also include endoprostheses implanted in a human or animal body, such as vascular grafts, stents, pacemaker leads, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts.

The invention provides a method for preparing a compound of Formula I:

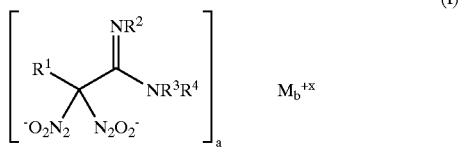

wherein $R^1$, $R^2$, $R^3$, and $R^4$ are described herein, comprising contacting a primary or secondary amine of the formula $NHR^3R^4$ with a nitric oxide-releasing imidate of Formula II:

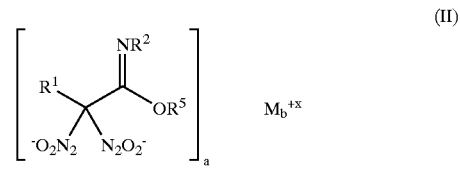

wherein $R^5$ is an unsubstituted or substituted $C_{1-12}$ straight chain alkyl, an unsubstituted or substituted $C_{3-12}$ branched chain alkyl, phenyl, or naphthyl; and $M^{+x}$ is a pharmaceutically acceptable cation, x is the valence of the cation, and a and b are the smallest integers that result in a neutral compound. Preferably, $R^5$ is an unsubstituted or substituted $C_{1-12}$ straight chain alkyl or an unsubstituted or substituted $C_{3-12}$ branched chain alkyl. More preferably, $R^5$ is methyl, ethyl, n-propyl, i-propyl, n-butyl, s-butyl, t-butyl, n-pentyl, i-pentyl, s-pentyl, neo-pentyl, or hexyl. Most preferably, $R^5$ is ethyl, n-propyl, i-propyl, or n-butyl. Additional information regarding compounds of Formula (II) can be found in U.S. patent application Ser. No. 09/950,162, filed Sep. 10, 2001, and is incorporated herein by reference.

It has been discovered that nitric oxide-releasing amidines can be produced from nitric oxide-releasing imidates of Formula II. In this method, the imidate is diazeniumdiolated and then this product, the nitric oxide-releasing imidate of Formula (II), is reacted with a primary ($NHR^3R^4$, in which $R^3$ is hydrogen) or secondary amine ($NHR^3R^4$, in which neither $R^3$ nor $R^4$ is hydrogen) to form a nitric oxide-releasing amidine. This process avoids subjecting the amine-containing compound to direct contact with the possible deleterious effects of nitric oxide gas. In some instances, both $R^3$ and $R^4$ can be hydrogen, therefore, the NO-releasing imidate is reacted with ammonia. The method provides access to a whole new class of compounds that heretofore were unstable to the diazeniumdiolation step.

In an illustrative embodiment shown below, the method for producing a compound of Formula I, comprises (a) contacting a nitrile of the formula $R^1CH_2CN$ with a metal alkoxide and an alcohol (e.g., NaOMe/HOMe); and (b) contacting the product of (a) with nitric oxide to form a diazeniumdiolated nitrile compound; (c) contacting the diazeniumdiolated nitrile compound with an additional alkoxide ($R^5OM$) and alcohol; and (d) contacting the product of (c) with a substituted or unsubstituted amine ($NHR^3R^4$) to form a compound of Formula (I), as illustrated to the following equation:

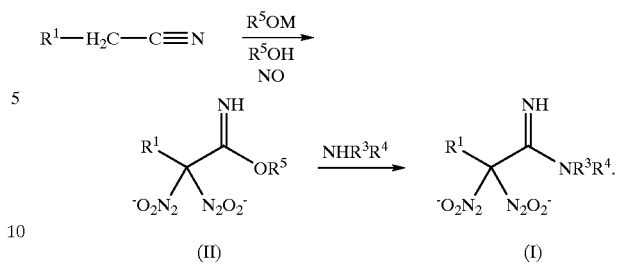

While typically the reaction to form the diazeniumdiolated imidates proceeds as described above, it will be appreciated by those skilled in the art that formation of the imidate may precede attachment of the diazeniumdiolate group. The exact sequence of the reaction is of no consequence in the invention and should in no way be construed to limit its scope. To prepare the diazeniumdiolates of the Formula (II), nitrile or imidate compounds are exposed to nitric oxide gas a suitable pressure. Preferably, the pressure is at least about 1 atm, and more preferably, it is at least about 2 atm.

The substituted or unsubstituted amine is preferably a primary (e.g., $NHR^3R^4$, in which $R^3$ is hydrogen) or secondary amine (e.g., $NHR^3R^4$, in which neither $R^3$ nor $R^4$ is hydrogen). Suitable primary and secondary amines include an organoamine (e.g., methylamine, ethylamine, benzylamine, adenosine, guanine, histamine, serotonin and guanosine, etc.), a drug containing a primary or secondary amine (e.g., ubenimex, valcyclovir), an amino acid (e.g., cysteine, lysine, tyrosine, thyroxine, etc.), a protein containing a primary or secondary amine, an enzyme containing a primary or secondary amine, tryptamine, glucosamine, mannosamine, mycosamine, sphingosine, thienamycin, penicillamine, and rimantadine.

Any combination of metal alkoxide/alcohol system that forms an imidate (i.e., a compound of Formula II) when exposed to a nitrile ($R^1CH_2CN$) and NO is within the scope of the invention. Suitable metal alkoxides are of the formula $MOR^5$, wherein M and $R^5$ are as discussed herein. Suitable alcohols are of the formula $HOR^5$, wherein $R^5$ is as discussed herein. The substituent $R^5$ of the metal alkoxide and the alcohol can be the same or different. Preferably, $R^5$ of the metal alkoxide and the alcohol are the same. The process according to the invention also includes the use of a metal hydroxide in combination with an alcohol (e.g., MOH/$HOR^5$). Combinations of metal hydroxides and metal alkoxides with an alcohol can also be used.

As is well known in the art, nitric oxide and compounds comprising $N_2O_2^-$ functional groups can have a wide range of utilities, in part because of the multifaceted role of nitric oxide in bioregulatory processes. Accordingly, the present invention also provides a composition, including a pharmaceutical composition, comprising a present inventive diazeniumdiolate of any of Formulae I and Ia. Preferably, the pharmaceutical composition additionally comprises a pharmaceutically acceptable carrier.

One skilled in the art will appreciate that suitable methods of administering a diazeniumdiolate composition of the present invention to an animal, such as a mammal, are available, and, although more than one route can be used to administer a particular composition, a particular route can provide a more immediate and more effective reaction than another route. Pharmaceutically acceptable carriers are also well known to those who are skilled in the art. The choice of carrier will be determined, in part, both by the particular composition and by the particular method used to administer the composition. Accordingly, there are a wide variety of suitable formulations of the pharmaceutical compositions of the present invention.

Formulations suitable for oral administration can consist of (a) liquid solutions, such as an effective amount of the diazeniumdiolate dissolved in diluents, such as water or saline, (b) capsules, sachets or tablets, each containing a predetermined amount of the active ingredient, as solids or granules, (c) suspensions in an appropriate liquid, and (d) suitable emulsions. Solutions may also be formulated using known preservatives for amidine-based nasal decongestants.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Compounds of the invention, alone or in combination with other suitable components, can be made into aerosol formulations to be administered via inhalation. These aerosol formulations can be placed into pressurized acceptable propellants, such as dichlorodifluoromethane, hydrofluorocarbons (e.g., HFC 134a and/or HFC 222), propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed (taking into consideration, at least, the rate of NO evolution, the extent of NO evolution, and the bioactivity of any decomposition products derived from the diazeniumdiolates) and the condition of the animal, as well as the body weight of the animal to be treated. The size of the dose also will be determined by the existence, nature, and extent of any adverse side effects that might accompany the administration of a particular composition. A suitable dosage for internal administration is 0.01 to 100 mg/kg per day. A suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%.

In view of the above, the present invention provides methods of using a nitric oxide-releasing amidine-derived diazeniumdiolate. In one embodiment, a method of treating an animal, such as a mammal (e.g., human), with a biological disorder treatable with nitric oxide, is provided. The method comprises administering to the animal, e.g., the mammal such as a human, in need thereof, an amount of an amidine-derived diazeniumdiolate sufficient to release a therapeutically effective amount of nitric oxide to treat the biological disorder in the animal. In this embodiment, "biological disorder" can be any biological disorder, including hypertension, cancer, restenosis, impotency, and a biological disorder due to a genetic defect or infection with an infectious agent, such as a virus, bacterium or parasite, as long as the disorder is treatable or preventable with nitric oxide.

With regard to the above, NO- and/or $NO^-$-releasing compounds derived from amidines are advantageous inasmuch as amidines are present in many already approved medicinal agents, e.g., tranquilizers, α-adrenergic antagonists, like phentolamine, and nasal decongestants. Specific examples include tolazoline and diazoxide. Other examples of amidine-containing compounds include methyl pyrimidine and 1,8-diamino octahydronaphthalene.

In another embodiment of a method of use, a method is provided for treating an animal, such as a mammal, for infection with, for example, a virus, a bacterium, or a parasite. The method comprises administering to the animal, e.g., the mammal, an amount of an inventive diazeniumdiolate sufficient to treat or prevent the infection in the animal.

In yet another embodiment, a method for treating an animal, such as a mammal, for cancer is provided. The method comprises administering to the animal, e.g., the mammal, an amount of an inventive diazeniumdiolate sufficient to prevent the growth or metastasis of the cancer in the animal or to render it more susceptible to radiation or chemotherapy.

In another embodiment, a method is provided for treating an inanimate object for the presence of a potentially infectious virus, bacterium, or parasite. The method comprises contacting the inanimate object with an amount of an inventive diazeniumdiolate sufficient to reduce the presence of the potentially infectious virus, bacterium or parasite. By "potentially infectious" is meant the capability of infecting an animal, such as a mammal.

It is contemplated that the diazeniumdiolates derived from amidines in accordance with the present invention can be used to coat prostheses, stents, and medical implants, such as breast implants, prior to surgical introduction into the body as a means of reducing the risk of solid state carcinogenesis associated therewith, or as a means of preventing adhesion of platelets to the implants. Additionally, the prostheses and implants can be manufactured using an amidine-derived diazeniumdiolate as an integral component of the starting materials. Medical devices incorporating an amidine-derived diazeniumdiolate provide an invaluable two-pronged approach to the treatment of many biological disorders, providing useful medical structures that also advantageously provide local release of NO.

The diazeniumdiolates derived from amidines also have utility in the in vitro study of NO biology.

Referring now to terminology used generically herein, the term "alkyl" implies a straight-chain or branched alkyl substituent containing from, for example, about 1 to about 12 carbon atoms, preferably from about 1 to about 8 carbon atoms, more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like. The alkyl group is preferably an alkyl group that promotes or enhances therapeutically desirable properties with respect to the compounds of the present invention, for example, anti-cancer or anti-microbial activity, metabolic stability, bioavailability, tissue distribution, improved pharmacokinetic properties, and the like, as will be appreciated by one of ordinary skill in the art.

The term "alkenyl," as used herein, means a linear alkenyl substituent containing from, for example, about 2 to about 12 carbon atoms (branched alkenyls are about 3 to about 12 carbons atoms), preferably from about 2 to about 8 carbon atoms (branched alkenyls are preferably from about 3 to about 8 carbon atoms), more preferably from about 3 to about 6 carbon atoms. Examples of such substituents include propenyl, isopropenyl, n-butenyl, sec-butenyl, isobutenyl, tert-butenyl, pentenyl, isopentenyl, hexenyl, octenyl, dodecenyl, and the like.

The term "halo" or "halogen," as used herein, means a substituent selected from Group VIIA, such as, for example, fluorine, bromine, chlorine, and iodine. Preferably, the halo is bromine or chlorine.

The term "aryl" refers to an unsubstituted or substituted aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms. It is understood that the term aryl applies to cyclic substituents that are planar and comprise 4n+2 π electrons, according to Hückel's Rule.

The term "cycloalkyl," as used herein, means a cyclic alkyl substituent containing from, for example, about 3 to about 8 carbon atoms, preferably from about 5 to about 8 carbon atoms, more preferably from about 5 to about 6 carbon atoms. Examples of such substituents include cyclopropyl, cyclobutyl, cyclopentyl, cyclohexyl, and the like.

The term "alkoxy" embraces linear or branched alkyl groups that are attached to divalent oxygen. The alkyl group is the same as described herein. Examples of such substituents include methoxy, ethoxy, t-butoxy, and the like. The aryl group is the same as described herein. The term "aryloxy" refers to substituents that have an aryl group attached to divalent oxygen. Examples of such substituents include phenoxy.

The term "alkylthio" as used herein, denotes a substituent with an alkyl or group directly attached to a divalent sulfur atom. The alkyl group is the same as described herein. Examples of such substituents include methylthio, ethylthio, and the like.

The term "alkylamino" refers to a secondary amine substituent with one hydrogen and one alkyl group directly attached to a trivalent nitrogen atom. The term "dialkylamino" refers to a tertiary amine substituent with two of the same or different alkyl groups directly attached to a trivalent nitrogen atom. The alkyl group is the same as described herein.

The term "trialkylsilyl" as utilized herein means three alkyl groups (the same or different) as defined herein, directly attached to a tetravalent silicon atom. Examples of such substituents include, for example, trimethylsilyl, methyl(dibutyl)silyl, tri-iso-propylsilyl, and the like.

The term "aralkyl" as utilized herein means alkyl as defined herein, wherein at least one hydrogen atom is replaced with an aryl substituent as defined herein. Aralkyls include, for example, benzyl, phenethyl, and substituents of the formula:

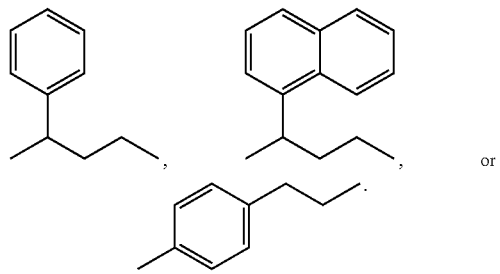

The term "heterocycloalkyl" means a cycloalkyl substituent as defined herein (including polycyclics), wherein at least one (e.g., 1 to 4, 1 to 3, 1 to 2, 1) carbon which defines the carbocyclic skeleton is substituted with a heteroatom such as, for example, O, N, or S, optionally comprising one or more double bond within the ring, provided the ring is not heteroaryl as defined herein. The heterocycloalkyl preferably has 3 to about 30 atoms (members) in the carbocyclic skeleton of each ring, preferably about 4 to about 7 atoms, more preferably 5 to 6 atoms. Examples of heterocycloalkyl substituents include epoxy, aziridyl, oxetanyl, tetrahydrofuranyl, dihydrofuranyl, piperadyl, piperidinyl, pyperazyl, piperazinyl, pyranyl, morpholinyl, and the like.

The term "heteroaryl" means a substituent defined by an aromatic heterocyclic ring, as is commonly understood in the art, including monocyclic and polyclic heteroaryls, wherein at least one (e.g., 1 to 4, 1 to 3, 1 to 2, 1) carbon which defines the carbocyclic skeleton is substituted with a heteroatom such as, for example, O, N, or S. Preferably, the heteroaryl contains from, for example, about 3 to about 30 atoms, preferably from about 5 to about 10 atoms, more preferably from about 5 to about 6 atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

It will also be appreciated that some polycyclic heterocyclic rings contain an aromatic ring and a non-aromatic ring. Examples of such polycyclic substituents include, for example, benzotetrahydrofuranyl, benzopyrrolidinyl, benzotetrahydrothiophenyl, and the like.

The following examples further illustrate the invention but should not be construed as in any way limiting its scope.

All melting points were determined on a hot stage and are uncorrected. The $^1$H NMR spectra were determined at 200 MHz with a Varian XL-200 spectrometer and the $^{13}$C NMR spectra were obtained at 50 MHz using the same instrument. The chemical shifts are expressed in δ values (ppm) relative to either tetramethylsilane or sodium 3-(trimethylsilyl) propionate-$d_4$ as internal standards. Elemental analyses were performed by Atlantic Microlabs, Inc. (Norcross, Ga.).

Except as noted here, all reagents and amines were obtained from Aldrich Chemical Company (Milwaukee, Wis.). Reaction solvents were Aldrich anhydrous grade but all others were reagent grade. Commercial grade nitric oxide was obtained from Matheson Gas Products and was used as received.

Reactions under pressure were conducted in standard glass hydrogenation bottles as previously described (Hrabie et al., *J. Org. Chem.* 58: 1472–1476 (1993)). The general directions are repeated here for completeness.

Given that stainless steel (SS) is required for prolonged exposure to NO gas and amines degrade most types of stoppers and gaskets, a specialized reactor modeled after the standard Parr 3911 hydrogenation apparatus (Parr Instrument Co., Moline, Ill.) was constructed. The reservoir was replaced by a type 304 SS gas sampling cylinder equipped with SS fittings (available from any "valve and fitting" plumbing supply company). The valves were diaphragm-seal packless type (Aldrich), and the pressure gauges were SS (Air Products). The usual Parr clamp and bottle system was employed but was connected to the gas reservoir via a Teflon tube and mounted to allow stirring with a magnetic stirrer.

EXAMPLE 1

This example describes the preparation of benzyl bis diazeniumdiolate ethoxy imidate.

Benzyl cyanide (3 mL, 0.025 moles) was dissolved in 30 mL of ethanol, and 2 equivalents of potassium ethoxide (4.30 g, 0.051 moles) were added. The reaction was run as described in Example 1. A light tan product was obtained. Yield 4.48 g, 50%; Mp 150° C. dec.; UV $\lambda_{max}$ ($\epsilon$) 262 nm (13.6 mM$^{-1}$ cm$^{-1}$); $^1$H NMR (300 MHz, D$_2$O): 1.27 (t, 3H), 4.26 (q, 2H), 7.47 ppm (s, 5H). Anal. Calcd for $C_{10}H_{11}N_5K_2O_5$:C, 33.42; H, 3.08; N, 19.49. Found: C, 33.48; H, 3.08; N, 19.17.

EXAMPLE 2

This example describes the conversion of an imidate diazeniumdiolate to a diazeniumdiolated amidine with N-acetyl cysteine.

A solution of PhC(N$_2$O$_2$Na)$_2$C(=NH)OC$_2$H$_5$ (57 mg in 1.5 ml 0.01 M NaOH), as prepared in Example 1, was treated with 50 mg of a neutralized solution of N-acetyl cysteine in 0.01 M NaOH. The solution was allowed to stir at room temperature overnight. To precipitate the diazeniumdiolated material, the solution was treated with methanol and ether. The product was filtered and, after air drying, a hard yellow solid was obtained which had a UV peak at 286 nm. Upon the addition of acid, the UV peak shifted to 264 nm.

EXAMPLE 3

This example describes the conversion of an imidate diazeniumdiolate to a diazeniumdiolated amidine with isobutylamine.

A solution of PhC(N$_2$O$_2$Na)$_2$C(=NH)OC$_2$H$_5$ (52 mg in 1.5 ml 0.01 M NaOH), as prepared in Example 1, was treated with 4 drops of isobutyl amine. The solution was allowed to stir at room temperature overnight. To precipitate the diazeniumdiolated material, the solution was treated with methanol and ether. The solution was filtered, and after air drying, a hard yellow solid was obtained which had a UV peak at 288 nm. Upon the addition of acid, the UV peak shifted to 260 nm.

EXAMPLE 4

This example describes the conversion of an imidate diazeniumdiolate to a diazeniumdiolated amidine with glutathione.

A solution of PhC(N$_2$O$_2$Na)$_2$C(=NH)OC$_2$H$_5$ (144 mg in 1.5 ml 0.01 M NaOH), as prepared in Example 1, was treated with neutralized glutathione (150 mg in 10 mM NaOH). The solution was allowed to stir at room tempera ture overnight. To precipitate the diazeniumdiolated material, the solution was treated with methanol and ether. The solution was filtered and, after air drying, an orange gummy solid was obtained which had a UV peak at 282 nm. Upon addition of acid, the UV peak shifted to 250 nm. When the compound was placed in 0.1 M NaOH, the compound had a UV peak at 274 nm.

EXAMPLE 5

This example describes the conversion of an imidate diazeniumdiolate to a diazeniumdiolated amidine with L-lysine methyl ester.

A solution of PhC(N$_2$O$_2$Na)$_2$C(=NH)OC$_2$H$_5$ (55 mg in 1.5 ml 0.01 M NaOH), as prepared in Example 1, was treated with neutralized L-lysine methyl ester (100 mg in 10 mM NaOH). The solution was allowed to stir at room temperature overnight. To precipitate the diazeniumdiolated material, the solution was treated with methanol and ether. The solution was filtered and, after air drying, an yellow gummy solid was obtained which had a UV peak at 282 nm. Upon addition of acid, the UV peak shifted to 250 nm.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of Formula (I):

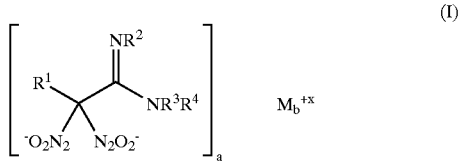

wherein $R^1$ is an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted $C_{1-12}$ alkoxy, halo, an unsubstituted or substituted benzyl, an unsubstituted or substituted phenyl, amino, an unsubstituted or substituted $C_{1-12}$ dialkylamino, an unsubstituted or substituted $C_{6-30}$ diarylamino, an unsubstituted or substituted tolyl, xylyl, anisyl, mesityl, an unsubstituted or substituted $C_{1-12}$ alkylthio, an unsubstituted or substituted $C_{1-12}$ alkyloxy, an unsubstituted or substituted phenoxy, an unsubstituted or substituted benzyloxy, or nitro;

$R^2$, $R^3$, and $R^4$ are selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted $C_{3-8}$ cycloalkyl, benzyl or substituted benzyl, and phenyl or substituted phenyl;

$M^{+x}$ is Na, x is 1, a is 1, and b is 2.

2. A compound of Formula (I):

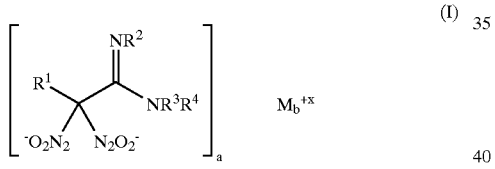

wherein $R^1$ is an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted $C_{1-12}$ alkoxy, halo, an unsubstituted or substituted benzyl, an unsubstituted or substituted phenyl, amino, an unsubstituted or substituted $C_{1-12}$ alkylamino, an unsubstituted or substituted $C_{6-30}$ arylamino, an unsubstituted or substituted $C_{1-12}$ dialkylamino, an unsubstituted or substituted $C_{6-30}$ diarylamino, an unsubstituted or substituted tolyl, xylyl, anisyl, mesityl, thio, an unsubstituted or substituted $C_{1-12}$ alkyithia, an unsubstituted or substituted $C_{1-12}$ alkyloxy, an unsubstituted or substituted phenoxy, an unsubstituted or substituted benzyloxy, or nitro;

$R^2$, $R^3$, and $R^4$ are selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted $C_{3-8}$ cycloalkyl, benzyl or substituted benzyl, and phenyl or substituted phenyl;

$M^{+x}$ is a pharmaceutically acceptable cation, x is the valence of the cation, and a and b are the smallest integers that result in a neutral compound.

3. The compound of claim 2, wherein each of $R^1$, $R^2$, $R^3$, and $R^4$ is optionally substituted each with 1 to 10 substituents independently selected from the group consisting of $C_{1-12}$ alkyl, $C_{6-30}$ aryl, $C_{1-12}$ alkoxy, $C_{1-12}$ aryloxy, benzyl, benzyloxy, $C_{6-30}$ arylamino, $C_{6-30}$ diarylamino, nitrile, tolyl, xylyl, mesityl, anisyl, $C_{1-12}$ alkylthio, $C_{1-12}$ trialkylsilyl, nitro, sulfonyl, nitrobenzyl, $C_{1-12}$ trialkylammonium, halo, bydroxy, thio, $C_{3-8}$ cycloalkyl, amino, $C_{1-12}$ alkylamino, $C_{1-12}$ dialkylamino and diazeniumdiolato.

4. The compound of claim 1 or 2, wherein $R^1$ is an unsubstituted or substituted aryl group.

5. The compound of claim 1 or 2, wherein $R^2$ is hydrogen.

6. The compound of claim 1 or 2, wherein $R^2$ and $R^3$ are hydrogen.

7. The compound of claim 1, wherein each of $R^1$, $R^2$, $R^3$, and $R^4$ is optionally substituted each with 1 to 10 substituents independently selected from the group consisting of $C_{1-12}$ alkyl, $C_{6-30}$ aryl, $C_{1-12}$ alkoxy, $C_{1-12}$ aryloxy, benzyl, benzyloxy, $C_{6-30}$ diarylamino, tolyl, xylyl, mesityl, anisyl, $C_{1-12}$ alkylthio, nitro, sulfonyl, nitrobenzyl, $C_{1-12}$ trialkylammonium, halo, hydroxy, $C_{3-8}$ cycloalkyl, amino, $C_{1-12}$ dialkylamino and diazeniumdiolato.

8. The compound of claim 1 or 2, wherein the compound is bound to a substrate.

9. The compound of claim 8, wherein the substrate is a medical device.

10. The compound of claim 9, wherein the medical device is selected from the group consisting of a stent, catheter, wound dressing, prosthesis, or implant.

11. A pharmaceutical composition comprising the compound of claim 1 or 2 and a pharmaceutically acceptable carrier.

12. A method for preparing the compound of claim 1 or 2, wherein the method comprises contacting a primary or secondary amine of the formula $NHR^3R^4$ with a compound of Formula II:

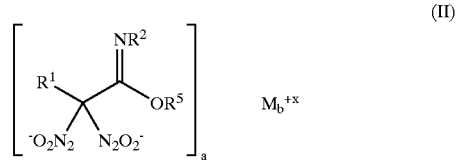

wherein $R^5$ is an unsubstituted or substituted $C_{1-12}$ straight chain alkyl, an unsubstituted or substituted $C_{3-12}$ branched chain alkyl, phenyl, or naphthyl.

13. A method for preparing a compound of claim 1 or 2, comprising (a) contacting a nitrile of the formula $R^1CH_2CN$ with a metal alkoxide and an alcohol; (b) contacting the product of (a) with nitric oxide to form a diazeniumdiolated nitrile compound; (c) contacting the diazeniumdiolated nitrile compound with an alkoxide; and (d) contacting the product of (c) with a substituted or unsubstituted amine.

14. The method of claim 13, wherein the substituted or unsubstituted amine is a primary or secondary amine.

15. A method for treating a biological disorder selected from the group consisting of restenosis, hypertension and impotency, by nitric oxide in a mammal in need thereof, comprising administering to the mammal the compound of claim 1 or 2 in an amount sufficient to treat said the biological disorder.

16. A method for treating a biological disorder selected from the group consisting of restenosis, hypertension and impotency, by nitric oxide in a mammal in need thereof, comprising administering to the mammal the composition of claim 11 in an amount sufficient to treat said the biological disorder.

* * * * *